United States Patent [19]

Basalay et al.

[11] 4,334,085
[45] Jun. 8, 1982

[54] TRANSAMINATION PROCESS FOR MANNICH PRODUCTS

[75] Inventors: Robert J. Basalay, Naperville; John H. Udelhofen, Wheaton, both of Ill.

[73] Assignee: Standard Oil Company (Indiana), Chicago, Ill.

[21] Appl. No.: 942,187

[22] Filed: Sep. 14, 1978

[51] Int. Cl.³ .............................................. C07C 87/28
[52] U.S. Cl. ................................... 564/367; 544/402; 544/404; 564/369; 564/389; 564/390
[58] Field of Search ..................... 260/268 R, 510.5 P, 260/570.9; 564/367, 369; 544/402, 404

[56] References Cited

U.S. PATENT DOCUMENTS 3,243,459 3/1966 O'Shea ......................... 260/570.9 X
3,646,110 2/1972 Eggensperger et al. ..... 260/570.5 X
3,736,357 5/1973 Piasek et al. .................. 260/570.9 X
4,022,836 5/1977 Hammen et al. ............ 260/570.5 X
4,054,422 10/1977 Garth .......................... 260/570.5 X

OTHER PUBLICATIONS

Houben-Weyl, "Methoden der Organischen Chemie", vol. 11, No. 1, pp. 259–261 (1957).

Primary Examiner—Robert V. Hines
Attorney, Agent, or Firm—William H. Magidson; William T. McClain

[57] ABSTRACT

A transamination process for producing Mannich products comprising reacting a polyamine with a substantially formaldehyde-free mononitrogen Mannich adduct.

8 Claims, No Drawings

TRANSAMINATION PROCESS FOR MANNICH PRODUCTS

This invention relates to a process for the preparation of Mannich products. More particularly, this invention relates to a transamination process for the preparation of Mannich products in which a mononitrogen Mannich adduct is formed from a Mannich reactive hydrocarbon containing an active or acidic hydrogen, for example an alkyl aromatic monohydroxy compound, a formaldehyde yielding reagent and a mononitrogen compound. After removing volatiles, the mononitrogen Mannich adduct is then reacted with a polyamine containing at least two nitrogen atoms which replaces the mononitrogen compound in the adduct to produce the Mannich product.

Considerable interest has developed in recent years in the use of Mannich condensation products to greatly enhance the properties of hydrocarbons. Mannich products improve (1) the ability of lubricants to suspend sludge, dirt, combustion byproducts etc. thereby preventing deposits on engine surfaces such as pistons, cylinder walls, bearings etc., and (2) the ability of fuels to prevent deposit formation on relatively cool carburetor surfaces and hot surfaces such as valves and intake passages. Mannich products also find beneficial service in many other functional fluids such as automatic transmission fluids etc.

Unpurified products of Mannich processes commonly contain small amounts of insoluble particle byproducts of the Mannich reaction which appear to be the high molecular weight condensation product of formaldehyde and polyamines. While the particles can be removed without harm to the properties of the purified Mannich product, the particles must be prevented from forming or must be removed, (e.g.), by filtering, prior to blending into functional fluids. Long chain carboxylic acids have been found to reduce solids formation during the Mannich reaction by solubilizing the particulate polyamine-formaldehyde condensation product by forming amide-type links. While the long hydrocarbon chain of the acid produces a particle free highly active product, the acids are relatively expensive. Alternatively, products can be filtered, or centrifuged to remove the particles. The viscosity of the Mannich product increases the time needed for filtration or centrifugation which can be a production bottleneck.

Examples of conventional processes for Mannich products are found in U.S. Pat. Nos. 3,539,633; 3,697,574; 3,704,308; 3,736,357; 3,751,365 and 3,872,019.

Accordingly there is a need for a process for producing active Mannich products which minimizes particle formation. The elimination of particle formation permits Mannich production without filtration, centrifugation or carboxylic acid treatment.

A primary object of the invention is to provide a Mannich process in which formaldehyde and polyamine do not react to produce solid insoluble particles. Another object of the invention is to eliminate the need for carboxylic acids or inefficient solids removal steps during processing. Another object of the invention is to produce a particle-free highly active Mannich product. Other objects appear hereinafter.

By transamination we mean reacting the mononitrogen Mannich adduct with a polyamine to exchange the polyamine for the mononitrogen compound. By mononitrogen Mannich adduct we mean a Mannich compound containing one or more moles of a mononitrogen compound.

We have found that the objects of this invention can be attained by a transamination process in which a polyamine is reacted with a substantially formaldehyde-free mononitrogen Mannich adduct. Particles are not formed by the condensation of mononitrogen compounds and formaldehyde, which forms only soluble mononitrogen-formaldehyde adducts and amino methylene substituents in the Mannich adduct. Once the Mannich adduct is prepared, any free formaldehyde is removed. The formaldehyde-free mononitrogen Mannich adduct is then reacted with the polyamine to replace the mononitrogen compound and form the polyamine Mannich product. The polyamine cannot form particles in the absence of formaldehyde.

Briefly the invention comprises producing a mononitrogen Mannich adduct using conventional processes, and reacting the formaldehyde-free mononitrogen Mannich adduct with a polyamine.

Conventional processes for the Mannich reaction comprise the reaction of a Mannich reactive compound, which is active in the reaction due to the presence of at least one active or acidic hydrogen. Commonly, either a substantially aliphatic hydrocarbon compound or a substantially aromatic hydrocarbon compound is used. Commonly, hydrogens adjacent to carbonyls, hydroxyls and other electron rich or donating functional groups are active in the Mannich reaction. In the Mannich reaction, a mononitrogen compound and a formaldehyde yielding reagent react to replace the acidic hydrogen with an amino-methylene group.

The mononitrogen compounds useful for forming the mononitrogen Mannich adduct are ammonia and amines containing one primary or secondary nitrogen atom. The mononitrogen Mannich adduct has little or no dispersancy. Each substituent on the nitrogen atom of the mononitrogen compound can be independently selected from hydrogen or alkyl groups having from one to about 20 carbon atoms. With a compound containing one nitrogen atom, high molecular weight insoluble particulate amineformaldehyde condensation products will not form. Stable particles are commonly formed only from polyamines containing multiple nitrogen atoms reacting with formaldehyde. The mononitrogen compound will condense only with a compound with an acidic hydrogen and formaldehyde forming generally at least one aminomethylene group per mononitrogen compound and forming one aminomethylene group per acidic hydrogen. Examples of suitable mononitrogen compounds are ammonia, methyl amine, ethyl amine, propyl amine, isopropyl amine, tertiary butylamine, hexyl amine, decyl amine, dodecyl amine, eicosyl amine. Other useful amines are dialkyl amines such as dimethyl amine, diethyl amine, methylethyl amine, methyl isopropyl amine, methyl dodecyl amine, methyl eicosyl amine, ethyl isopropyl amine, ethyl butyl amine. Tertiary amines cannot be used since tertiary amines contain no removable hydrogen atom on the nitrogen for reaction with the formaldehyde.

In the Mannich reaction an aminomethylene group replaces an acidic proton on a substantially hydrocarbon compound. Since the particle forming problems result from the polyamine-formaldehyde side reactions, the nature of the hydrocarbon used in the Mannich reaction is of lesser importance. The minimum required for reaction is a carbon atom in the molecule with at least one acidic hydrogen which is replaceable with an aminomethylene group during the Mannich reaction. The substantially hydrocarbon compound can have various substituents on the compound, including hydroxyl, carbonyl, carboxyl, organometallic nitrogen containing, halogen containing, sulfur containing, phosphorus containing, organometallic, boron containing, etc. substituents. Commonly commercial Mannich products are prepared from alkyl monohydroxy aromatic compound or alkyl monohydroxy aromatic compounds derivatized with sulfur, halogens, etc., oxidized olefinic polymers such as ethylene-propylene copolymers, and ethylene-propylene-diene copolymers, alkyl benzene sulfonic acids and others. Hydrocarbyl substituted high molecular weight phenols, naphthols, etc. will undergo the Mannich reaction. The high molecular weight substituted phenols are obtained by alkylation of phenol, with $C_4$ to $C_{500}$ polypropenes, polybutenes, or polymers (molecular weight about 200 to 6000) containing propene, butene, and other olefin monomers. The comonomers polymerized with propenes or butenes may be partly aliphatic, but can also contain nonaliphatic groups such as benzene substituted monomers, e.g., styrene, alphamethylstyrene, divinylbenzene, etc. The polymers resulting from the polymerization of the above-mentioned monomers are substantially aliphatic hydrocarbon polymers and thus the resulting alkylated aromatic monohydroxy compounds are substantially aliphatic hydrocarbons. Hydrocarbons which undergo the Mannich reaction are well known to those skilled in the art. U.S. Pat. Nos. to Culbertson 3,872,019 and West 4,011,380 which are hereby incorporated by reference disclose oxidized polymers and Mannich products derived therefrom.

Formaldehyde can be used as pure formaldehyde or can be derived from suitable formaldehyde-yielding compounds. Suitable formaldehyde yielding compounds such as aqueous and alcoholic solutions of formaldehyde (formalin), paraformaldehyde, trioxane, trioxymethylene, etc. can be used.

Regardless of the Mannich reaction compound used and means used to form the Mannich adduct, any free formaldehyde present must be substantially removed prior to transamination. Preferably, the volatile formaldehyde can easily be stripped with a heated inert gas.

The Mannich adduct, now formaldehyde-free, reacts with a polyamine, displacing the mononitrogen compound forming the polyamine Mannich. Polyamines are amines containing at least two nitrogen atoms separated by at least an ethylene group where at least one nitrogen atom is hydrogen bonded. One amino nitrogen forms an amino methylene bond to the phenol, the other amino nitrogen forms a polar group at some distance from the aromatic monohydroxy nucleus. This distance appears to produce the dispersancy function. Examples of such amines are polyalkene polyamines of the formula:

$NH_2(A-NH)_nH$ wherein A is an alkylene group having from 2 to 6 carbon atoms and n is a number from 1 to 6. Examples of polyalkene polyamines are: ethylenediamine, hexamethylenediamine, diethylenetriamine, triethylenetetramine, tetraethylenepentamine, tripropylenetetramine, etc. Other polyamines are the "Duomenes" made by Armak Chemical having the formula $RHNCH_2CH_2CH_2NH_2$ wherein R is a hydrocarbyl having 2 to 25 carbon atoms. Examples of other dispersant-forming polyamines are bis(aminopropyl)-ethylenediamine, bis(aminopropyl)-piperazine and bis(aminopropyl)-methylamine etc.

In somewhat greater detail the mononitrogen Mannich adduct is produced by conventional technology. Mononitrogen Mannich adducts are made by the reaction of mononitrogen compound, formaldehyde and a Mannich reactive hydrocarbon having an acidic proton such as an alkyl aromatic monohydroxy compound, oxidized copolymers etc. The mononitrogen Mannich adduct can be formed by the reaction of a Mannich reactive hydrocarbon with at least one acidic hydrogen such as a substantially aliphatic or substantially aromatic compound, oxidized polymer etc. and either (1) a mononitrogen compound and a formaldehyde-yielding compound or (2) the condensation reaction product of a mononitrogen compound and a formaldehyde-yielding compound.

In the case where the Mannich reactive hydrocarbon is reacted with a mononitrogen compound and the formaldehyde to form the Mannich adduct, about 0.1 to about 5 moles of mononitrogen compound per mole of Mannich reactive hydrocarbon is added along with about 0.1 to 5 moles of formaldehyde-yielding reagent. The reaction forming the mononitrogen Mannich adduct can be conducted at a temperature from about ambient (20° C.) to about 300° C. Preferably the reaction mixture is held at a temperature of about 160° C. for a period of time from about 1 hour to about 6 hours. At the end of the reaction, the mixture is heated and blown with an inert gas to strip water, excess amine and formaldehyde.

In the case that the Mannich reactive hydrocarbon is reacted with condensation reaction product of a mononitrogen compound and the formaldehyde-yielding reagent to form the mononitrogen Mannich adduct, the mononitrogen compound first reacts with formaldehyde to form condensation product. Formaldehyde is reacted with from about 0.5 to 5.0 moles of mononitrogen per mole of formaldehyde. This reaction is generally acid catalyzed, and an equilibrium between the reaction product and starting materials is quickly established. The reaction can be run at ambient (20° C.) to about 200° C. For example, 6 moles of formaldehyde and 4 moles of ammonia react to form hexamethylenetetraamine, liberating water. The hexamethylenetetramine product has a high melting point, is stable at room temperature and is well known to those skilled in the art. Hexamethylenetetramethylene contains 6 equivalents of formaldehyde. Also, 2 equivalents of a secondary amine can react with one equivalent of formaldehyde releasing water. These types of amine-formaldehyde condensation products are stable and are easily reacted to form the mononitrogen Mannich adduct and removed by stripping. In the reaction between the Mannich reactive hydrocarbon and the mononitrogen compound-formaldehyde condensation product, the hydrocarbon is reacted with from about 0.1 mole equivalents to about 5 mole equivalents of the mononitrogen compound-formaldehyde condensation product. The reaction between the mononitrogen-formaldehyde condensation product and the Mannich reactive hydrocarbon can be conducted at a temperature from about ambient (20° C.) to about 300° C.; preferably about 160° C. The reaction can be performed for about 1 to 6 hours. At the end of the reaction, the mixture is heated and blown with an inert gas to remove water, formaldehyde, mononitrogen and other volatiles.

To the mononitrogen Mannich adduct formed above is added about 0.1 to about 5 moles of the polyamine per mole of reactive hydrocarbon present. The mixture of the mononitrogen Mannich adduct and the polyamine is heated to a temperature from about ambient (20° C.) to about 300° C., preferably about 160° C. The reaction is conducted for a period of time from about 1 to 6 hours. At the end of the reaction, the mixture is stripped of water, amine and other volatiles.

Generally, not all of the mononitrogen compound can be displaced in the reaction. Typically about 80–95 mole % of the amine is recovered. Mononitrogen compounds with substituents of low molecular weight are more labile in the presence of the polyamine. As the molecular weight of the substituents of the mononitrogen compound increase the recovery of the mononitrogen compounds decrease.

A benefit of using hexamethylenetetramine (HMTA) is that ammonia which is the mononitrogen compound precursor, excess HMTA etc. are volatilized at the stripping temperature and substantially completely removed along with small amounts of formaldehyde by-product of the transamination if present. Also hexamethylenetetramine, the ammonia-formaldehyde condensation product, does not require a preliminary reaction of the hexamethylenetetraamine and the Mannich reactive hydrocarbon. A mixture of the reactive hydrocarbon, the polyamine and the hexamethylenetetramethylene can be immediately formed and reacted. The mixture of Mannich reactive hydrocarbon, polyamine and hexamethylenetetramine in the mole ratios discussed above can be mixed and heated to a temperature from about ambient (20° C.) to about 300° C. and reacted for a period of time from about 1 hour to about 6 hours. The mixture at the end of the reaction is then stripped at an elevated temperature (150° C.–200° C.) to remove volatiles.

The transamination reaction producing the Mannich product contemplates the use of various catalysts such as hydrocarbon sulfonic acid, acetic acid and others. About 0.1 to about 2 wt.% of an alkylbenzene sulfonic acid based on the Mannich reactive hydrocarbon, can be used. About 0.02 to 0.5 moles of acetic acid per mole of Mannich reactive hydrocarbon can be used. The product after stripping is ready for use.

An aqueous solution of about 1–50 wt.% hexamethylenetetramine can be used. The solution of hexamethylenetetramine will produce some resin-forming formaldehyde by hydrolysis, but the relatively slow rate of hydrolysis of HMTA compared to rate of condensation and transamination to form Mannich product allows only minor amounts of resin formation.

The mononitrogen Mannich adduct reaction and the transamination reaction can be performed in both continuous or batch reaction. In batch processes, the reactant or reactants in solution or neat may be added to the other reactants in a suitable vessel. In continuous processing two components in solution or solventless can be charged to different or countercurrent process zones or the same reaction zones, e.g., the upper end of a vertical zone maintained at a suitable elevated temperature. The product is commonly withdrawn from the other and into purification strippers.

Solvents useful in the adduct and transmination reactions are common aliphatic and aromatic processing solvents. Examples of aliphatic type solvents are hexane, heptane, ligroin, petroleum ether, lubricating oils, etc. Examples of aromatic solvents are benzene, toluene, $C_9+$ aromatic stream, etc. Preferably the Mannich product is made in a hydrocarbon such as kerosene or lubricating oil. The ultimate fate of the Mannich dispersants is a fuel or lubricant oil blend. Thus the production of the additive in a hydrocarbon fuel or lubricant base is beneficial.

The following examples are illustrative and should not be construed as limiting the scope of the invention.

EXAMPLE I

To a 5 liter round bottom flask equipped with a stirrer and a nitrogen atmosphere, was charged 1,667.0 grams of polybutene substituted phenol, molecular weight about 1600 (50% active in oil), (0.5 mols), 600 grams of 5 W oil, and 74 grams of diethylamine (1.0 moles). The flask was heated with stirring to a temperature of 66° C. To the solution was added 83 milliliters of formalin (1.1 moles $CH_2O$). The reaction mixture was held at 66° C. for 1 hour under the nitrogen atmosphere. The mixture was then heated to 155° C. while volatiles, including water, excess amine, and formaldehyde were removed by the nitrogen stream. The product contained 0.26 percent nitrogen, indicating that the phenol was substituted with one aminomethylene group. To 235 grams of the phenol adduct above (0.05 moles) in the same vessel was added 9.5 gms (0.05 moles) of tetraethylenepentamine (TEPA). The mixture was heated to 155° C. and blown with a nitrogen stream. The nitrogen stream was contacted with an acid trap and the diethylamine displaced was collected.

EXAMPLE II

Example I was repeated with 10 gm of bisaminopropylpiperazine (0.05 mole) (BAPP).

EXAMPLE III

Example I was repeated with 7.4 gm of triethylene tetramine (0.05 mole )(TETA).

EXAMPLE IV

To a 3 liter round bottom flask equipped with a stirrer and a nitrogen atmosphere was charged 833 grams of polybutyl phenol (0.25 moles), 300 grams of 5 weight oil, 44 grams of tetraethylenepentamine (TEPA) (0.23 moles), and 12 grams of hexamethylenetetramine (0.086 moles) equivalent to 0.516 moles of formaldehyde. The mixture was treated with 28 milliliters of water, and heated to 155° C. for 3 hours. During the reaction a nitrogen stream was blown through the reaction mixture and the ammonia and amine was collected in an acid trap.

EXAMPLE V

Example IV was repeated with 1 wt.% of a sulfonic acid catalyst based on the total mixture.

EXAMPLE VI

Example IV was repeated with 0.25 moles of acetic acid catalyst.

EXAMPLE VII

To a 3 liter round bottom flask equipped with a stirrer and a nitrogen atmosphere, 833 grams of polybutyl phenol (0.25 moles), 300 grams of 5 weight oil, 44 grams tetraethylene pentamine (0.23 moles) and 11 grams of an alkyl benzene sulfonic acid molecular weight 450, 50 percent active in 5 W oil, were charged. To this mixture various amounts of hexamethylenetetramine, as shown below, were added and the mixture was heated to 66° C. The mixture was held at 66° C. for 1 hour before heating to 155° C. with a nitrogen stream to remove volatiles. At the end of the stripping the product was filtered and collected.

| Polybutyl Phenol/Hexamethylene Tetramine Mole Ratio | |
| --- | --- |
| a | 3:1 |
| b | 3:1 |
| c | 9:2 |
| d | 6:1 |
| e* | 6:1 |
| f* | 9:2 |
| g* | 3:1 |
| h* | 3:1 |

*Hexamethylenetetramine added is 30% by weight in water.

EXAMPLE VIII

To a 3 liter round bottom flask equipped with a stirrer and nitrogen atmosphere was charged 833 gms of polybutyl phenol (0.25 moles), 300 gms 5 W oil, 44 gms of tetraethylene-pentamine and 15.5 gms formaldehyde. The mixture was heated to 66° C. for 1 hour then stripped at 155° C. for 3 hours with nitrogen.

TABLE I

BENCH TESTS OF PRODUCTS OF EXAMPLE VII

| | Spot Dispersancy Test | Hot Tube Test |
| --- | --- | --- |
| a | 87.5 | 5 |
| b | 88.7 | 5 |
| c | 88.9 | 4.2 |
| d | 72.4 | 1.5 |
| e | 80.5 | 1.5 |
| f | 85.1 | 4 |
| g | 88.9 | 4 |
| h | 87.7 | 4.5 |

TABLE II

BENCH TEST OF THE MANNICH PRODUCT MADE BY THE CATALYZED REACTION

| Example | Catalyst | Spot Dispersancy Test | Hot Tube Test |
| --- | --- | --- | --- |
| IV | Water | 44.4 | — |
| V | Polypropyl benzene sulfuric acid | 87.5 | 5 |
| VI | Acetic acid | 79.2 | 4.2 |

TABLE III

TRANSMINATION OF THE DIETHYLAMINO METHYLENE PHENOL REACTION MOLES OF DIETHYLAMINE PRODUCT BY VARIOUS AMINES

| Example | Amine | Displaced | Spot Dispersancy Test | Hot Tube Test |
| --- | --- | --- | --- | --- |
| I | TEPA | 0.485 | 87.9 | 1.5 |
| II | BAPP | 0.525 | 91.3 | 1.5 |
| III | TETA | 0.570 | 82.4 | 1.5 |

TABLE IV

CAT 1-H TEST (120 HRS)

| Formulation** | Top Groove Fill | Weighted Total Deposits |
| --- | --- | --- |
| Example V | 32 | 96 (ave. two tests) |
| Conventional Mannich Product | 34 | 83 (ave. four tests) |

| **Dispersant | 4.5 (vol)% |
| --- | --- |
| Zn diisoamyldithiophosphate | 1.6 |
| Polymethacrylate VI improver | 5.8 |
| Antifoam | 0.1 |
| Base 0:1 | Balance |

TABLE V

SEDIMENT AND RESIN FORMATION

| | SEDIMENT VOL. % |
| --- | --- |
| EXAMPLE IV | <0.01 |
| EXAMPLE VIII | 0.11 |

TABLE VI

VC ENGINE TEST***

| Test | EXAMPLE V | CONVENTIONAL MANNICH |
| --- | --- | --- |
| Average Sludge | 9.51 | 9.39 |
| Average Varnish | 8.68 | 8.60 |
| Piston Varnish | 8.48 | 8.24 |

| ***Formulation | |
| --- | --- |
| Isooctylphenoxytetraethoxy ethanol | 0.1% (vol) |
| Sulfurized Calcium phenate | 1.01% |
| Overbased Magnesium Sulfonate | 1.26% |
| Zinc diisoamyl dithiophosphate | 1.6% |
| Polymethacrylate VI improver | 5.8% |
| Base oil | Balance |

The Spot Dispersancy Test gives a measure of the oil's ability to disperse sludge and varnish. In the Spot Dispersancy Test, a dispersant is mixed with an amount of Ford VC sludge oil and is incubated at 300° F. for 16 hours and 3-10 drops of this mixture are dropped onto a standard white blotter paper producing a sludgeoil spot. After 24 hours, the diameter of the sludge and the oil rings are measured. Dispersancy is reflected by the ability of an oil to keep sludge in suspension. Thus, dispersancy will be reflected by the difference in diameters of the sludge and oil rings. High dispersancy is reflected by the sludge ring being nearly as wide as the oil ring. A rating (SDT Rating) is given by the diameter of the sludge ring divided by the diameter of the oil ring, and multiplied by 100. A high numerical rating indicates good dispersancy.

The hot tube test is a determination of the oxidation and varnish resistant properties of an oil package. A measured quantity of oil is metered into a 2 mm heated glass tube through which heated air or heated nitrogen dioxide is blown through the tube. The oil is consumed in the test and the deposits in the tube are measured. The tubes are rated from zero through ten. Zero being a heavy black opaque deposit, and 10, perfectly clean.

An examination of the tables shows the improvement in performance in processing and lubrication of these novel Mannich additives. Table I displays the Bench test high dispersancy and adequate hot tube test and the relative equivalence of products made from HMTA in water and neat HMTA. Table II displays the relative properties of Mannich products made with various catalysts. Table III shows the diethylamine is indeed displaced from the adduct in agreement with the proposed mechanism for the reaction. Tables Iv and VI display the Engine tests, showing equivalence of the Mannich products and the conventional Mannich products. Table V shows the reduction in particulate sediment using the improved transamination procedure.

Since many embodiments of this invention may be made and many changes may be made in the embodiments described, the foregoing is to be interpreted as illustrative only and our invention is defined by the claims appended hereafter.

I claim:

1. A transamination process for Mannich products comprising the reaction of a polyamine comprising at least two nitrogen atoms separated by at least an ethylene group with a substantially formaldehyde-free mononitrogen Mannich adduct.

2. The transamination process of claim 1 wherein the substantially formaldehye-free Mannich adduct is the product of the process comprising reacting a formaldehyde-yielding compound, a mononitrogen compound selected from the group consisting of ammonia, primary amines and secondary amines, and a hydrocarbon compound having at least one acidic hydrogen, and removing substantially all volatiles.

3. The process of claim 2 wherein the formaldehyde-yielding reagent and the mononitrogen compound are reacted separately producing a condensation product prior to producing the Mannich adduct.

4. The process of claim 3 wherein the polyamine and the condensation product are simultaneously reacted with the hydrocarbon compound having at least one acidic hydrogen.

5. The process of claim 3 wherein the condensation reaction product is hexamethylene tetramine.

6. The process of claim 2 wherein the hydrocarbon compound having at least one acidic hydrogen is selected from the group consisting of an alkyl substituted phenol having a molecular weight from about 300 to 6000 and an oxidized olefinic polymer.

7. The process of claim 2 wherein the mononitrogen compound is selected from the group consisting of dimethyl amine, diethyl amine, methylethyl amine, and ammonia.

8. The process of claim 1 wherein the polyamine is selected from the group consisting of bis(aminopropyl)-piperazine, bis(aminopropyl)-ethylene diamine, bis-(aminopropyl)-methylamine and an amine of the formula $$NH_2(A-NH)_nH$$

wherein A is an alkylene group having 2 to 6 carbon atoms and n is a number from 1 to 6.

* * * * *

UNITED STATES PATENT OFFICE
CERTIFICATE OF CORRECTION

Patent No. 4,334,085                    Dated June 8, 1982

Inventor(s) Robert J. Basalay and John H. Udelhofen

It is certified that error appears in the above-identified patent and that said Letters Patent are hereby corrected as shown below:

Column 5, line 67, "transmination" should read --transamination--.

Column 7, line 58, "TRANSMINATION" should read --TRANSAMINATION--.

Column 8, line 42, "sludgeoil" should read --sludge-oil--.

Column 9, line 2, "Iv" should read --IV--.

Column 9, line 19, "formaldehye-free" should read --formaldehyde-free--.

Signed and Sealed this

Twenty-eighth Day of December 1982

[SEAL]

Attest:

GERALD J. MOSSINGHOFF

Attesting Officer    Commissioner of Patents and Trademarks